United States Patent
Suzuki et al.

(10) Patent No.: US 8,702,850 B2
(45) Date of Patent: Apr. 22, 2014

(54) ELECTRIC DEVICE WITH AIR CLEANING FUNCTION

(75) Inventors: Daisuke Suzuki, Moriguchi (JP); Masahiro Iseki, Moriguchi (JP); Keiko Kurokawa, Moriguchi (JP); Mineo Ikematsu, Moriguchi (JP); Hiroyuki Umezawa, Moriguchi (JP); Yoshiaki Noguchi, Moriguchi (JP)

(73) Assignee: Sanyo Electric Co., Ltd., Moriguchi-Shi, Osaka-Fu (JP)

( * ) Notice: Subject to any disclaimer, the term of this patent is extended or adjusted under 35 U.S.C. 154(b) by 571 days.

(21) Appl. No.: 13/003,617

(22) PCT Filed: Jul. 15, 2009

(86) PCT No.: PCT/JP2009/063138
§ 371 (c)(1),
(2), (4) Date: Mar. 9, 2011

(87) PCT Pub. No.: WO2010/008089
PCT Pub. Date: Jan. 21, 2010

(65) Prior Publication Data
US 2011/0179951 A1 Jul. 28, 2011

(30) Foreign Application Priority Data
Jul. 16, 2008 (JP) ................. 2008-185026
Mar. 24, 2009 (JP) ................. 2009-072101

(51) Int. Cl.
*B03C 3/014* (2006.01)
(52) U.S. Cl.
USPC ........... 96/27; 95/67; 95/71; 95/72; 96/52; 96/74; 96/289; 261/92

(58) Field of Classification Search
USPC .............. 96/27, 41, 42, 52, 74, 286–289; 95/64–67, 71, 72; 261/92; 204/212, 204/213
See application file for complete search history.

(56) References Cited

U.S. PATENT DOCUMENTS 3,370,403 A * 2/1968 D'Elia et al. ............... 96/19
3,601,313 A * 8/1971 Berg ........................ 239/2.1
3,967,940 A * 7/1976 Hirano et al. ................ 96/52

(Continued)

FOREIGN PATENT DOCUMENTS

EP 1 728 521 12/2006
EP 1 760 412 3/2007

(Continued)

OTHER PUBLICATIONS

Supplementary European Search Report for EP 09 79 8013, dated Jan. 10, 2012.

*Primary Examiner* — Richard L Chiesa
(74) *Attorney, Agent, or Firm* — Preti Flaherty Beliveau & Pachios LLP

(57) ABSTRACT

In an electric device (1), an air inlet (3), a gas-liquid contact portion (5), a water collecting portion (6) and an air outlet (7) are arranged in sequential order from upstream of an air duct (2). In a water storage portion (8) the gas-liquid contact portion (5) is dipped and the water collected thereby is stored. An electrolyzing portion (9) generates the electrolyzed water (4) containing an active oxygen species by electrolyzing the water stored in the water storage portion (8). As a result, a compact electric device with an air cleaning function is provided at low cost that is capable of generating water containing an active oxygen species without requiring additional water feed and without generating a by-product.

6 Claims, 4 Drawing Sheets

(56) References Cited

U.S. PATENT DOCUMENTS

| | | | |
|---|---|---|---|
| 4,308,037 A * | 12/1981 | Meissner et al. | 95/71 |
| 5,518,525 A * | 5/1996 | Steed | 95/58 |
| 5,704,954 A * | 1/1998 | Takagi | 96/286 |
| 2005/0087071 A1* | 4/2005 | Petz et al. | 96/52 |
| 2008/0028936 A1* | 2/2008 | Takahashi et al. | 96/25 |
| 2008/0072757 A1 | 3/2008 | Dobashi | |
| 2011/0017066 A1* | 1/2011 | Takeuchi et al. | 96/52 |

FOREIGN PATENT DOCUMENTS

| | | | |
|---|---|---|---|
| EP | 1 892 483 | 2/2008 | |
| EP | 2 033 708 | 3/2009 | |
| JP | 60-177614 A * | 9/1985 | 96/41 |
| JP | 07-214080 | 8/1995 | |
| JP | 2001-091146 | 4/2001 | |
| JP | 2002-035097 | 2/2002 | |
| JP | 2006-110403 | 4/2006 | |
| JP | 2007-064534 | 3/2007 | |
| JP | 2007-101023 | 4/2007 | |
| JP | 2007-175313 | 7/2007 | |
| JP | 2007-312988 | 12/2007 | |
| JP | 2008-000590 | 1/2008 | |
| JP | 2008-79724 | 4/2008 | |
| WO | WO 2009/110660 | 9/2009 | |

* cited by examiner

ELECTRIC DEVICE WITH AIR CLEANING FUNCTION

TECHNICAL FIELD

The present invention relates to electric devices of various types including air cleaners, air conditioners, humidifiers, and refrigerators. The present invention more specifically relates to an electric device with an air cleaning function.

BACKGROUND ART

Ozone ($O_3$), that is an isotope of oxygen, is known to have strong sterilizing power, deodorizing power, oxidizing power, and bleaching power. Technology that uses ozone gas for sterilization and deodorization of inside refrigerators has been developed in recent years by taking advantage of these characteristics (see, for example, Patent Literature 1). Ozone water containing ozone dissolved therein is used in sterilizing devices placed at factories or hospitals, in cleaning devices of semiconductor wafers, and others.

Ozone is generated by various known techniques, of which the most widely applied one employs corona discharge or silent discharge. An ozone generator employing such a discharge technique is used in the refrigerator disclosed in Patent Literature 1. When ozone water is used, the following way is generally employed in which ozone gas generated by an ozone generator such as that described above is dissolved in water by bubbling or ejection technique, thereby generating ozone water.

By way of example, the device disclosed in Patent Literature 2 includes a circulation filtering unit for bathwater that uses ozone. In this device, ozone gas generated by an ozone generator and bathwater are stirred in a pump, so that ozone is dissolved more quickly in the bathwater.

However, the ozone generator employing a discharge technique has problems such as instability of the amount of generated ozone under the influence of humidity and the like, and generation of an undesirable by-product such as nitrogen oxides. The technique of generating ozone water by dissolving ozone gas in water is likely to increase the scale of a device. Accordingly, this technique is hard to apply in home appliances in respects of size and cost.

In addition, ozone affects adverse effects on human bodies. Accordingly, except for special usages in factories or hospitals, for example, it has been difficult to take advantage of its strong sterilizing power and deodorizing power mentioned above.

In light of the problems described above, the following air conditioner (Patent Literature 3), floor-standing air disinfection device (Patent Literature 4), electric device (Patent Literature 5), and others have been suggested. The aforementioned air conditioner is provided with an ozone water generator to avoid generation of slime in a drain pan. The aforementioned floor-standing air disinfection device removes a harmful substance by making gas-liquid contact between ozone water generated by an ozone water generator and external air. In the aforementioned electric device, humidity, temperature and the like are controlled by air intake. Ozone water generated by ozone water generating means is made finer or vaporized, and is then discharged into the air, thereby removing and exhausting a harmful substance.

PRIOR ART DOCUMENT

Patent Literatures

[Patent Literature 1] Japanese Patent Application Laid-Open No. 2001-91146

[Patent Literature 2] Japanese Patent Application Laid-Open No. Hei. 7-214080 (1995)

[Patent Literature 3] Japanese Patent Application Laid-Open No. 2007-64534

[Patent Literature 4] Japanese Patent Application Laid-Open No. 2007-175313

[Patent Literature 5] Japanese Patent Application Laid-Open No. 2007-101023

SUMMARY OF INVENTION

Problems to be Solved by Invention

By the Patent Literatures 3 and 4 described above, ozone water is used to remove a harmful substance. However, in either case, ozone water and air are together ejected, and therefore ozone water should always be generated by electrolysis of new water continuously fed to the ozone water generator. In the result, there were problems of a large amount of water consumed while requiring great time and labor, leading to a cost increase.

In the Patent Literature 5 described above, generated ozone water is made finer or vaporized, and is then discharged into the air, thereby removing a harmful substance. This requires a unit for making water finer or vaporizing water, water discharging means, and the like, leading to a problem of cost increase. Further, consuming ozone water necessitates continuous generation of new ozone water, leading to a large amount of water consumed. Thus, cost is increased in terms of the two aspects.

The present invention has been made to solve the foregoing problems. A main object of the present invention is to provide a compact electric device with an air cleaning function at low cost that is capable of generating electrolyzed water such as ozone water containing an active oxygen species without additionally feeding water and without generating a by-product.

Means For Solving Problems

An electric device recited in a first aspect of the present invention includes: an air inlet through which air is taken in; a gas-liquid contact portion for making gas-liquid contact between the air taken in and electrolyzed water to purify the air; a water collecting portion for collecting moisture in the air after the gas-liquid contact; an air outlet through which the air in which the moisture was collected is ejected, wherein the air inlet, the gas-liquid contact portion, the water collecting portion, and the air outlet are arranged in sequential order from upstream of an air duct; a water storage portion in which the gas-liquid contact portion is dipped and in which the water collected by the water collecting portion is stored; and an electrolyzing portion for generating the electrolyzed water containing an active oxygen species by electrolyzing the water stored in the water storage portion.

According to an electric device recited in a second aspect of the present invention, in the electric device recited in the first aspect, the water collecting portion includes: a moisture absorber for absorbing moisture in the air after the gas-liquid contact; a releasing portion for heating the moisture absorbed by the moisture absorber to release the moisture; and a cooling portion for cooling and condensing the released moisture with the air after the gas-liquid contact to collect the moisture. The water collected after the cooling and condensation is stored in the water storage portion.

According to an electric device recited in a third aspect of the present invention, the electric device recited in the first or second aspects includes a controlling portion for maintaining the water level of the water stored in the water storage portion within a predetermined range.

According to an electric device recited in a fourth aspect of the present invention, the electric device recited in any of the first to third aspects includes active oxygen species removing means for removing an active oxygen species from air ejected through the air outlet.

According to an electric device recited in a fifth aspect of the present invention, in the electric device recited in any of the first to fourth aspects, the water collecting portion uses a Peltier element, the air after the gas-liquid contact comes into contact with a heat absorbing portion of the Peltier element to condense and collect moisture in the air, and the air from which the moisture was collected comes into contact with a heat generating portion of the Peltier element and is controlled in temperature, where necessary, and which is thereafter ejected.

An air cleaner recited in a sixth aspect of the present invention includes: an air inlet through which air is taken in; a gas-liquid contact portion for making gas-liquid contact between the air taken in and electrolyzed water to purify the air; a water collecting portion for collecting moisture in the air after the gas-liquid contact; air blowing means for transferring the air from which the moisture was collected to an air outlet; an air outlet through which the air is ejected, wherein the air inlet, the gas-liquid contact portion, the water collecting portion, the air-blowing means, and the air outlet are arranged in sequential order from upstream of an air duct; a water storage portion in which the water collected by the water collecting portion is stored; a pump for feeding the water stored in the water storage portion to the gas-liquid contact portion; and an electrolyzing portion for generating the electrolyzed water containing an active oxygen species by electrolyzing the water stored in the water storage portion.

According to an air cleaner recited in a seventh aspect of the present invention, in the air cleaner recited in the sixth aspect, the water collecting portion includes: a moisture absorber for absorbing moisture in the air after the gas-liquid contact; a releasing portion for heating the moisture absorbed by the moisture absorber to release the moisture; and a cooling portion for cooling and condensing the released moisture with the air after the gas-liquid contact to collect the moisture. The water collected after the cooling and condensation is stored in the water storage portion.

According to an air cleaner recited in an eighth aspect of the present invention, the air cleaner recited in the sixth or seventh aspects includes a sustained-release material holding portion for holding a sustained-release material that gradually releases chlorine ions by contacting with moisture. The water collected by the water collecting portion is given the chlorine ions to increase in conductivity in the sustained-release material holding portion, and is then fed into the water storage portion.

According to an air cleaner recited in a ninth aspect of the present invention, the air cleaner recited in the eighth aspect includes conductivity detecting means for determining the conductivity of the water stored in the water storage portion. If the conductivity of the water in the water storage portion determined by the conductivity detecting means is equal to, or lower than, a predetermined level, the water collecting means collects water, and feeds water containing chlorine ions released from the sustained-release material holding portion into the water storage portion.

According to an air cleaner recited in a tenth aspect of the present invention, the air cleaner recited in any one of the sixth to ninth aspects includes a water level sensor in the water storage portion. The water level sensor maintains the water level of the water stored in the water storage portion within a predetermined range.

Effects of Invention

The electric device recited a first aspect of the present invention includes: an air inlet through which air is taken in; a gas-liquid contact portion for making gas-liquid contact between the air taken in and electrolyzed water to purify the air; a water collecting portion for collecting moisture in the air after the gas-liquid contact; an air outlet through which the air in which the moisture was collected is ejected, wherein the air inlet, the gas-liquid contact portion, the water collecting portion, and the air outlet are arranged in sequential order from upstream of an air duct; a water storage portion in which the gas-liquid contact portion is dipped and in which the water collected by the water collecting portion is stored; and an electrolyzing portion for generating the electrolyzed water containing an active oxygen species by electrolyzing the water stored in the water storage portion.

In this structure, air taken through the air inlet is collected by the water collecting portion (employing a system using a moisture absorber, an electronic system using a Peltier element, a refrigeration circuit system using a refrigeration cycle, and the like). The collected water is stored in the water storage portion, and the water stored in the water storage portion is electrolyzed to generate the electrolyzed water containing an active oxygen species such as ozone. The air taken in comes into gas-liquid contact with the electrolyzed water at the gas-liquid contact portion to purify the air, and then the purified air is ejected. This produces a remarkable effect since air is cleaned without requiring additional water feed and without generating a by-product, and the size and cost reductions, and long-term stable use are realized. Further, increasing humidity by making gas-liquid contact of the air taken in leads to a higher rate of water collection even in the case of low humidity as a result of a small amount of moisture in the air taken in through the air inlet, for example. Also, the gas-liquid contact between the air and the electrolyzed water at the gas-liquid contact portion causes moisture to evaporate, and resultant evaporation heat cools the air. Thus, if the cooled air is used for water collection at the water collecting portion, this produces a remarkable effect since a rate of water collection is further increased to a higher level.

According to the electric device recited in a second aspect of the present invention, in the electric device recited in the first aspect, the water collecting portion includes: a moisture absorber for absorbing moisture in the air after the gas-liquid contact; a releasing portion for heating the moisture absorbed by the moisture absorber to release the moisture; and a cooling portion for cooling and condensing the released moisture with the air after the gas-liquid contact to collect the moisture. The water collected after the cooling and condensation is stored in the water storage portion.

In this structure, the moisture absorber wet with sufficient moisture is recovered, for example, in the following way for its reuse. First, the moisture absorber is driven by a motor to rotate, so that the moisture absorber moves to the releasing portion. Then, the moisture absorber is heated by heating means such as a heater to discharge the moisture into air. The air containing the discharged moisture is cooled by the cooling portion to cool and condense the moisture, thereby collecting water. The collected water is stored in the water storage portion. Accordingly, moisture in the air taken in is efficiently collected, and the air is cleaned without requiring additional water feed. Further, the cooling portion cools the air heated with absorption heat generated when the moisture absorber absorbs water. This also produces further remarkable effect since a discomfort due to increasing temperature of the ejected air is reduced or relieved.

According to the electric device recited in a third aspect of the present invention, the electric device recited in the first or second aspects includes a controlling portion for maintaining the water level of the water stored in the water storage portion within a predetermined range.

The controlling portion controls the number of revolutions of a rotor for causing the moisture absorber to rotate, input to a heater, the amount of water to be collected, and the like in response to a water level. This also produces a remarkable effect since air is purified stably and reliably at the gas-liquid contact portion.

According to the electric device recited in a fourth aspect of the present invention, the electric device recited in any of the first to third aspects includes active oxygen species removing means for removing an active oxygen species from air ejected through the air outlet.

If a sensor determines that an active oxygen species such as ozone of a concentration equal to or greater than a predetermined level is contained in the ejected air, the active oxygen species removing means is started in response to a signal from a controlling device. Thus, the level of the active oxygen species such as ozone is reduced to a safe level, or the active oxygen species is removed completely. This produces another remarkable effect in terms of improved safety.

According to the electric device recited in a fifth aspect of the present invention, in the electric device recited in any of the first to fourth aspects, the water collecting portion uses a Peltier element, the air after the gas-liquid contact comes into contact with a heat absorbing portion of the Peltier element to condense and collect moisture in the air, and the air from which the moisture was collected comes into contact with a heat generating portion of the Peltier element and is controlled in temperature, where necessary, and which is thereafter ejected.

Supplying electricity to the Peltier element causes one end of the Peltier element to function as the heat absorbing portion, and the other end of the Peltier element to function as the heat generating portion. By using this feature, when air comes into contact with the heat absorbing portion, moisture in the air is condensed and collected. Then, the air from which the moisture was collected comes into contact with the heat generating portion and is controlled in temperature, where necessary, and which is thereafter ejected. This also produces further remarkable effects since energy efficiency is enhanced furthermore, and size reduction and further cost reduction are accomplished.

The air cleaner recited in a sixth aspect of the present invention includes: an air inlet through which air is taken in; a gas-liquid contact portion for making gas-liquid contact between the air taken in and electrolyzed water to purify the air; a water collecting portion for collecting moisture in the air after the gas-liquid contact; air blowing means for transferring the air from which the moisture is collected to an air outlet; an air outlet through which the air is ejected, wherein the air inlet, the gas-liquid contact portion, the water collecting portion, the air-blowing means, and the air outlet are arranged in sequential order from upstream of an air duct; a water storage portion in which the water collected by the water collecting portion is stored; a pump for feeding the water stored in the water storage portion to the gas-liquid contact portion; and an electrolyzing portion for generating the electrolyzed water containing an active oxygen species by electrolyzing the water stored in the water storage portion.

Thus, a remarkable effect is produced since a compact air cleaner is provided at low cost that is capable of generating electrolyzed water such as ozone water containing an active oxygen species without requiring additional water feed and without generating a by-product.

According to the air cleaner recited in a seventh aspect of the present invention, in the air cleaner recited in the sixth aspect, the water collecting portion includes: a moisture absorber for absorbing moisture in the air after the gas-liquid contact; a releasing portion for heating the moisture absorbed by the moisture absorber to release the moisture; and a cooling portion for cooling and condensing the released moisture with the air after the gas-liquid contact to collect the moisture. The water collected after the cooling and condensation is stored in the water storage portion.

In this structure, the moisture absorber wet with sufficient moisture is recovered, for example, in the following way for its reuse. First, the moisture absorber is driven by a motor to rotate, so that the moisture absorber moves to the releasing portion. Then, the moisture absorber is heated by heating means such as a heater to discharge the moisture into air. The air containing the discharged moisture is cooled by the cooling portion to cool and condense the moisture, thereby collecting water. The collected water is stored in the water storage portion. Accordingly, moisture in the air taken in is efficiently collected, and the air is cleaned without requiring additional water feed. Further, the cooling portion cools the air heated with absorption heat generated when the moisture absorber absorbs water. This also produces a remarkable effect since discomfort due to temperature increase of ejected air is reduced or relieved.

According to the air cleaner recited in an eighth aspect of the present invention, the air cleaner recited in the sixth or seventh aspects includes a sustained-release material holding portion for holding a sustained-release material that gradually releases chlorine ions after contacting moisture. The water collected by the water collecting portion is given the chlorine ions to increase in conductivity in the sustained-release material holding portion, and is then fed into the water storage portion.

Condensed water obtained from air comes into contact with the sustained-release material to be given chlorine ions. This produces further remarkable effect since the condensed water increases in conductivity to reduce a voltage required for electrolysis, while efficiency of ozone generation is enhanced.

According to the air cleaner recited in a ninth aspect of the present invention, the air cleaner recited in the eight aspect includes conductivity detecting means for determining the conductivity of the water stored in the water storage portion. If the conductivity of the water in the water storage portion determined by the conductivity detecting means is equal to, or lower than, a predetermined level, the water collecting means collects water, and feeds water containing chlorine ions released from the sustained-release material holding portion into the water storage portion. This further produces a remarkable effect since chlorine ions are given precisely to condensed water as the need arises.

According to the air cleaner recited in a tenth aspect of the present invention, the air cleaner recited in any one of the sixth to ninth aspects includes a water level sensor in the water storage portion for maintaining the water level of the water stored in the water storage portion within a predetermined range. The water level sensor controls the number of revolutions of a rotor for causing the moisture absorber to rotate, input to a heater, the amount of water to be collected, and the like in response to a water level. This also produces a remarkable effect since air is purified stably and reliably at the gas-liquid contact portion.

DESCRIPTION OF REFERENCE NUMERALS

Figure 1:
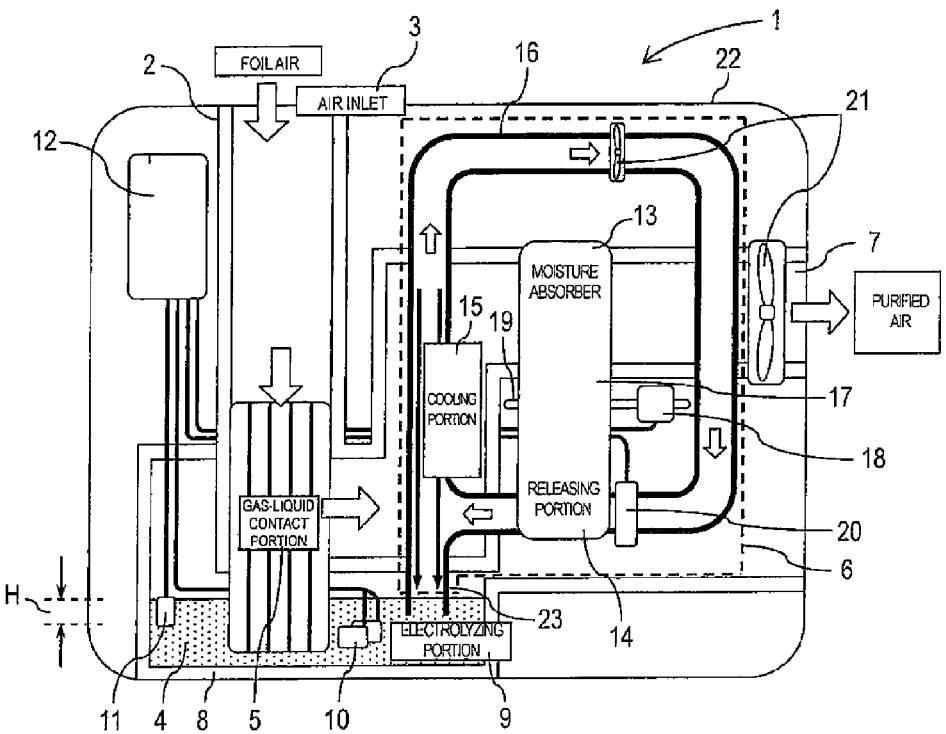
FIG. 1 is an explanatory view of an embodiment of an electric device of the present invention.

1, 1A electric device
1B air cleaner
2 duct
3 air inlet
4 electrolyzed water
5 gas-liquid contact portion
6 water collecting portion
7 air outlet
8 water storage portion
9 electrolyzing portion
10 active oxygen species generating electrodes (electrolyzing portion)
11 water level sensor
12 controlling portion
13 moisture absorber
14 releasing portion
15 cooling portion
16 air circulation duct
17 rotor
18 motor
19 rotary shaft
20 heater
21 fan
21A fan (air blowing means)
21B fan
22 housing
23, 24 coupling path
30 Peltier element
31 heat absorbing portion
32 cooling fin
33 heat generating portion
34 heat dissipation portion
40 sustained-release material
41 sustained-release material holding portion
42 pump

BEST MODE FOR CARRYING OUT INVENTION

Embodiments of an electric device of the present invention will be described in detail with reference to drawings.
(First Embodiment of Electric Device of Present Invention)

FIG. 1 is an explanatory view of an embodiment of an electric device of the present invention.

As shown in FIG. 1, an electric device 1 of the present invention includes: an air inlet 3 through which foil air is taken in to travel in a direction indicated by blank arrows; a gas-liquid contact portion 5 for making gas-liquid contact between the air taken in and electrolyzed water 4 to purify the air; a water collecting portion 6 for collecting moisture in the air after the gas-liquid contact; and an air outlet 7 through which the purified air the moisture in which was collected is ejected. The air inlet 3, the gas-liquid contact portion 5, the water collecting portion 6, and the air outlet 7 are arranged in sequential order from upstream of an air duct 2.

The electric device 1 of the present invention further includes: a water storage portion 8 in which the collected water is stored; and an electrolyzing portion 9 for generating the electrolyzed water 4 containing an active oxygen species by electrolyzing the water stored in the water storage portion 8.

The electrolyzing portion 9 includes active oxygen species generating electrodes 10 placed in the water in the water storage portion 8 in order to electrolyze water to generate the electrolyzed water 4.

A water level sensor 11 is provided in the electrolyzed water 4 in the water storage portion 8 in order to maintain the level of the water in the water storage portion 8 within a range H of between predetermined upper and lower limits.

The upper limit is such that exceeding the height of the upper limit results in a fear of an overflow. The lower limit is such that failing to reach the height of the lower limit results in a fear that electrolysis will be made impossible and cannot be conducted well due to insufficient immersion of the electrodes 10 in the water, or a fear of imperfect air purification due to insufficient gas-liquid contact at the gas-liquid contact portion 5.

Reference numeral 12 indicates a controlling portion. In response to a signal from the water level sensor 11, the controlling portion 12 controls the number of revolutions of a rotor 17 for causing a moisture absorber 13 described later to rotate, the number of rotations of the gas-liquid contact portion 5, energization of the electrodes 10, input to a heater 20, the amount of water to be collected, and the like. As a result, air is purified stably and reliably at the gas-liquid contact portion 5.

The water collecting portion 6 will be described next.

The water collecting portion 6 includes an air circulation duct 16. The air circulation duct 16 causes moisture absorbed by the moisture absorber 13 to be released at a releasing portion 14, and causes a cooling portion 15 to cool and condense air containing the released moisture to collect the moisture in the air. The air circulation duct 16 thereafter causes the air to circulate in the direction indicated by blank arrows. Reference numeral 21 indicates fans for air transfer.

More specifically, the water collecting portion 6 transfers air after gas-liquid contact at the gas-liquid contact portion 5 through the air duct 2 in the direction of blank arrows. Further, the water collecting portion 6 includes the moisture absorber 13 rotatably placed at an appropriate position in the air duct 2, and the releasing portion 14. The moisture absorber 13 absorbs moisture in the transferred air. The releasing portion 14 causes the moisture absorber 13 to rotate to move to the position of the releasing portion 14, and heats the moisture absorbed by the moisture absorber 13 to release the moisture, thereby recovering the moisture absorber 13.

The cooling portion 15 of the air circulation duct cools the air circulation duct 16 from outside with air that is cooled as a result of generation of evaporation heat generated when moisture in the air evaporates after the air makes gas-liquid contact with the electrolyzed water 4 at the gas-liquid contact portion 5. Then, the cooling portion 15 cools the air containing moisture released at the releasing portion 14 to condense the moisture in the air.

The condensed water flows downward along the inner wall of the air circulation duct 16, and which is then fed into the water storage portion 8 through a coupling path 23. Here, the coupling path 23 is connected to a predetermined position in the air circulation duct 16, and is placed such that one end of the coupling path 23 is inserted in the water storage portion 8. The stored water is electrolyzed in the water storage portion 8 to generate the electrolyzed water 4 containing an active oxygen species.

For cooling by the cooling portion 15, the air circulation duct 16 is cooled from outside with air that is cooled as a result of generation of evaporation heat generated when moisture in the air evaporates after the air makes gas-liquid contact with the electrolyzed water at the gas-liquid contact portion 5. In addition to this system, an electronic system using a Peltier element, or a refrigeration circuit system using a refrigeration cycle may be used in combination, for example. Or, at least one the foregoing systems may be used.

The moisture absorber 13 and the releasing portion 14 are provided at their predetermined positions in the rotor 17. The moisture absorber 13 and the releasing portion 14 are driven by a motor 18 to rotate about a rotary shaft 19.

In order for the moisture absorber 13 that absorbs moisture to move to the releasing portion 14 shown in FIG. 1, the motor 18 is actuated to cause the rotor 17 to rotate about the rotary shaft 19, thereby moving the moisture absorber 13 to the releasing portion 14. The moisture absorber 13 having reached the releasing portion is heated by the heater 20, so that the moisture absorber 13 releases the moisture, and is recovered accordingly. Then, the motor 18 is actuated again to cause the rotor 17 to rotate about the rotary shaft 19, thereby moving the recovered moisture absorber 13 to the predetermined position shown in FIG. 1 at which the moisture absorber 13 is reused.

Reference numeral 21 indicates fans for air transfer. Reference numeral 22 indicates a housing in which the constituting portions are integrally placed at their predetermined positions.

The moisture absorber used in the present invention is not specifically limited, as long as it absorbs moisture in air, and it becomes reusable, for example, by heating. Specific examples of the moisture absorber used in the present invention include zeolite. Commercially available products may be used as well.

An active oxygen species mentioned here means oxygen with oxidation activity higher than that of normal oxygen, and its associated material. The active oxygen species includes not only what is called narrowly-defined active oxygen such as superoxide anion, singlet oxygen, hydroxyl radical and hydrogen peroxide, but also what is called broadly-defined active oxygen such as ozone and hypohalous acid.

(Description of Example of Water Electrolysis)

The electric device 1 of the present invention is configured such that air is taken in from outside space such as space in a room or closed space into the electric device 1 through the air inlet 3. The air taken in comes into gas-liquid contact with the electrolyzed water 4 at the gas-liquid contact portion 5 to purify the air. Then, moisture in the purified air is collected by the water collecting portion 6. The collected water is electrolyzed in the water storage portion 8 to generate the electrolyzed water 4 containing an active oxygen species such as ozone, and the purified air is ejected through the air outlet 7.

If the active oxygen species generating electrodes are ozone electrodes, on condition that water of a predetermined amount or more, more specifically water of an amount that allows immersion of the electrodes 10 (a platinum cathode and a metal oxide anode, for example) or more is stored in the water storage portion 8, a not-shown power supply energizes the electrodes 10 in response to a signal from the controlling portion 12. Then, water electrolysis is started, so that the reaction shown by the following formula (1) occurs to generate ozone, so that the electrolyzed water (ozone water) 4 containing the generated ozone dissolved therein is generated in the water storage portion 8:

$$3H_2O \rightarrow O_3 + 6H^+ + 6e^- \tag{1}$$

The gas-liquid contact portion 5 has a gas-liquid contact member (what is called disk-type gas-liquid contact member) with a plurality of disks that are spaced a certain interval apart, and at least some of which is dipped in the ozone water 4 in the water storage portion 8. The plurality of disks are caused to rotate integrally by not-shown driving means about a not-shown rotary shaft. When the multiple disks are caused to rotate, each one of the disks draws up the ozone water 4, so that the surface of each disk gets wet. A gas-liquid contact member of the gas-liquid contact portion 5 is publicly known. In the present invention, a publicly known gas-liquid contact member (such as that used in LAQULIA MIST SV-DK807 available from Mitsubishi Electric Corporation) may be employed.

When the air taken in through the air inlet 3 is fed to the gas-liquid contact portion 5, the air enters the gaps between the plurality of disks wet with the ozone water 4, thereby making gas-liquid contact with the electrolyzed water 4. The gas-liquid contact between the air and the ozone water 4 realizes disinfection (sterilization) and deodorization (odor removal) of the air, and removal of a suspended matter and a hazardous matter from the air, thereby purifying the air. The purified air is transferred in the direction indicated by arrows from the gas-liquid contact portion 5.

The electric device 1 of the present invention uses condensed water collected from air to generate ozone water, thereby eliminating the need, for example, for water feed by a user. This makes a water feeding unit unnecessary while saving time and labor.

A gas-liquid contact member of the gas-liquid contact portion 5 is not limited to that described above. A gas-liquid contact member of a porous structure (porous structure with communicatively coupled pores, for example) made of a material not deteriorated seriously by electrolyzed water is applicable. Examples of the material include polyolefin resins, PET resins, vinyl chloride resins, fluorinated resins, and ceramics resins. More specifically, the applicable gas-liquid contact member is such that it has a wide gas contact area, that it has a surface capable of getting wet with electrolyzed water, that it has a resistance to clogging, and that it allows air purification by making gas-liquid contact between air taken in from outside space and the electrolyzed water.

(Description of Example of Electrolysis by Addition of Tap Water)

The present invention can also conduct electrolysis by adding tap water into the water storage portion 8.

Tap water is added through not-shown tap water feeding means into the water storage portion 8. Then, on condition that water of a predetermined amount or more, more specifically water of an amount that allows immersion of the electrodes 10 or more is stored in the water storage portion 8, a not-shown power supply energizes the electrodes 10 in response to a signal from the controlling portion 12. This implements water electrolysis to cause reactions shown by the following formulas (2) to (5), thereby generating an active oxygen species. As a result, the electrolyzed water 4 containing the generated active oxygen species dissolved therein is generated in the water storage portion 8.

If the active oxygen species generating electrodes are hypochlorous acid generating electrodes, the electrodes 10 are electrode plates the bases of which are made of Ti (titanium), and the coating layers of which are made of Ir (iridium) and Pt (platinum), for example. A current of a value of from some milliamperes to several dozen milliamperes/cm$^2$ (square centimeter) in terms of current density is applied to the electrodes, thereby generating free residual chlorine of a predetermined concentration (1 mg (milligram)/1 (liter), for example). The following reaction occurs at the cathode:

$$4H^+ + 4e^- + (4OH^-) \rightarrow 2H_2 + (4OH^-) \quad (2)$$

The following reaction occurs at the anode:

$$2H_2O \rightarrow 4H^+ + O_2 + 4e^- \quad (3)$$

At the same time, chlorine ions in water (preliminarily contained in tap water) generates reaction as follows:

$$2Cl^- \rightarrow Cl_2 + 2e^- \quad (4)$$

$Cl_2$ in the formula (4) further reacts with water as follows:

$$Cl_2 + H_2O \rightarrow HClO + HCl \quad (5)$$

This structure generates HClO (hypochlorous acid) having strong sterilizing power through the energization between the electrodes 10. Air taken in through the air inlet 3 is fed to the gas-liquid contact portion 5 dipped in the electrolyzed water 4 containing the generated CHlO (hypochlorous acid) dissolved therein. This prevents propagation of bacteria, and inactivates viruses and allergens floating in air passing through the gas-liquid contact portion 5. Further, an odor reacts with hypochlorous acid in the electrolyzed water 4 to be ionized and then dissolved while air passes through the gas-liquid contact portion 5. Thus, the odor is removed from the air to deodorize the air.

In the foregoing description, electrolysis of condensed and collected water, and electrolysis by adding tap water are shown as examples. In the present invention, these ways of electrolysis may be applied alone, or may be applied in combination. Combined use thereof more effectively prevents propagation of bacteria, more effectively inactivates viruses and allergens, and realizes more effective deodorization.

Second Embodiment of Electric Device of Present Invention

Figure 2:
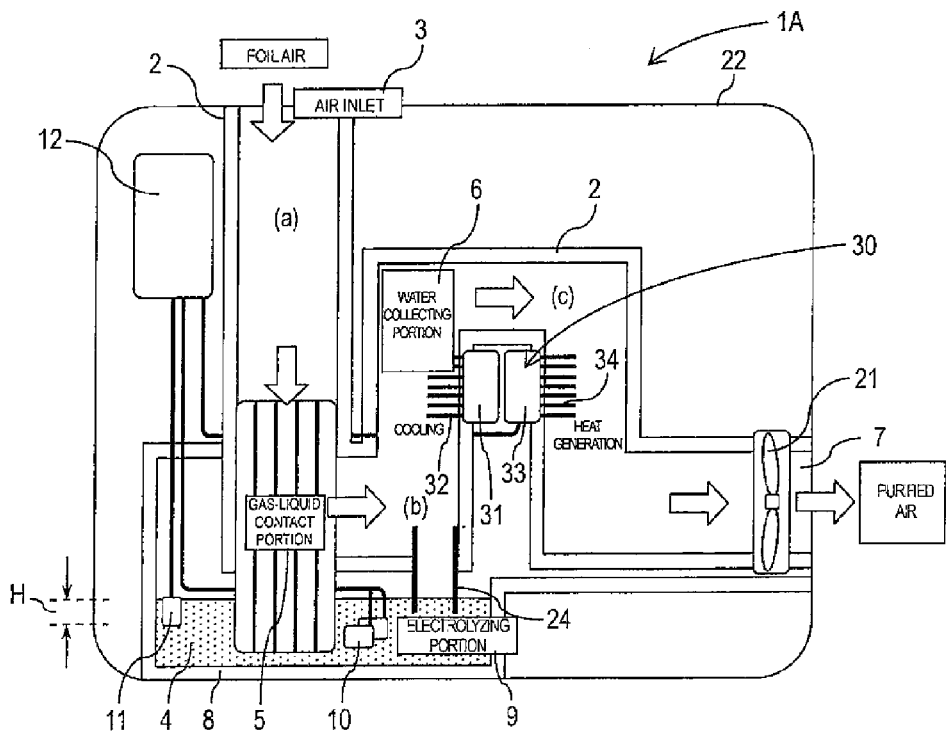
FIG. 2 is an explanatory view of a different embodiment of the electric device of the present invention.

FIG. 2 is an explanatory view of a different electric device 1A of the present invention where a water collecting portion uses a Peltier element.

As shown in FIG. 2, the electric device 1A of the present invention includes: an air inlet 3 through which foil air is taken in to travel in a direction indicated by arrows; a gas-liquid contact portion 5 for making gas-liquid contact between the air taken in and electrolyzed water 4 to purify the air; a water collecting portion 6 with a Peltier element 30 for collecting moisture in the air after the gas-liquid contact; and an air outlet 7 through which the purified air the moisture in which was collected is ejected. The air inlet 3, the gas-liquid contact portion 5, the water collecting portion 6, and the air outlet 7 are arranged in sequential order from upstream of an air duct 2.

The electric device 1A of the present invention further includes: a water storage portion 8 in which the collected water is stored; and an electrolyzing portion 9 for generating the electrolyzed water 4 containing an active oxygen species by electrolyzing the water stored in the water storage portion 8.

The electrolyzing portion 9 includes active oxygen species generating electrodes 10 placed in the water in the water storage portion 8 in order to electrolyze water to generate the electrolyzed water 4.

A water level sensor 11 is provided in the electrolyzed water 4 in the water storage portion 8 in order to maintain the level of the water in the water storage portion 8 within a range H of between predetermined upper and lower limits.

The upper limit is such that exceeding the height of the upper limit results in a fear of an overflow. The lower limit is such that failing to reach the height of the lower limit results in a fear that electrolysis will be made impossible and cannot be conducted well due to insufficient immersion of the electrodes 10 in the water, or a fear of imperfect air purification due to insufficient gas-liquid contact at the gas-liquid contact portion 5.

Reference numeral 12 indicates a controller. In response to a signal from the water level sensor 11, the controlling portion 12 controls the number of rotations of the gas-liquid contact portion 5, energization of the electrodes 10, energization of the Peltier element 30, the amount of water to be collected, and the like. As a result, air is purified stably and reliably at the gas-liquid contact portion 5.

The water collecting portion 6 is described next.

The water collecting portion 6 is constructed of the Peltier element 30. Air after gas-liquid contact at the gas-liquid contact portion 5 is transferred through the air duct 2 in the direction indicated by blank arrows. Then, the air comes into contact with cooling fins 32 coupled to a heat absorbing portion 31 of the Peltier element 30 to condense moisture in the air. The condensed water flows downward in a direction indicated by black arrows, and is then carried to the water storage portion 8 through a coupling path 24. The coupling path 24 is connected to a predetermined position in the air duct 2, and is placed such that one end of the coupling path 24 is inserted in the water storage portion 8. The stored water is electrolyzed in the water storage portion 8 to generate the electrolyzed water 4 containing an active oxygen species.

As shown by blank arrows, the air from which the moisture was collected comes into contact with heat dissipation fins 34 coupled to a heat generating portion 33 of the Peltier element 30, thereby heating the air. The heated air is subjected to temperature control by the controlling portion 12, and is ejected thereafter.

(Description of Example of Condensed and Collected Water)

Air is taken in from outside space such as space in a room or closed space into the electric device 1A through the air inlet 3. The air taken in comes into gas-liquid contact with the electrolyzed water 4 at the gas-liquid contact portion 5 to purify the air. Then, the air after the gas-liquid contact at the gas-liquid contact portion 5 is transferred through the air duct 2. The transferred air comes into contact with the cooling fins coupled to the heat absorbing portion 31 of the Peltier element 30, thereby condensing moisture in the air. The condensed water flows downward into the water storage portion 8, in which the condensed water is electrolyzed to generate the electrolyzed water 4 containing an active oxygen species.

The air from which the moisture was collected comes into contact with the heat dissipation fins 34 coupled to the heat generating portion 33 of the Peltier element 30, thereby heating the air. The heated air is subjected to temperature control by the controlling portion 12, and is ejected thereafter.

If the active oxygen species generating electrodes are ozone electrodes, on condition that water of a predetermined amount or more, more specifically water of an amount that allows immersion of the electrodes 10 (a platinum cathode and a metal oxide anode, for example) or more is stored in the water storage portion 8, a not-shown power supply energizes the electrodes 10 in response to a signal from the controlling portion 12. Then, water electrolysis is started, so that the reaction shown by the foregoing formula (1) occurs to generate ozone. Then, the electrolyzed water (ozone water) 4 containing the generated ozone dissolved therein is generated in the water storage portion 8.

As already described, a gas-liquid contact member of the gas-liquid contact portion 5 is publicly known. In the present invention, a publicly known gas-liquid contact member may be employed.

When the air taken in from outside space is fed to the gas-liquid contact portion 5, the air enters gaps between a plurality of disks wet with the ozone water 4, thereby making gas-liquid contact with the electrolyzed water 4. The gas-liquid contact between the air and the ozone water 4 realizes disinfection (sterilization) and deodorization (odor removal) of the air, and removal of a suspended matter and a hazardous matter from the air, thereby purifying the air.

In the foregoing description of the embodiment, electrolysis of condensed and collected water for obtaining the ozone water 4 is shown as an example. Electrolysis may also be conducted by adding tap water. Or, these two ways of electrolysis may be applied in combination. Combined use thereof more effectively prevents propagation of bacteria, more effectively inactivates viruses and allergens, and realizes more effective deodorization.

Reference numeral 21 indicates a fan for air transfer, and reference numeral 22 indicates a housing.

The electric device 1A of the present invention uses condensed water collected from air to generate ozone water, thereby eliminating the need, for example, for water feed by a user. This makes a water feeding unit unnecessary while saving time and labor.

An exemplary structure of the Peltier element 30 used in the present invention is as follows. N-type semiconductor and p-type semiconductor are used as thermoelectric converting materials of an n-type thermoelectric converter and a p-type thermoelectric converter, respectively. Electrodes are placed on upper and lower end portions of each of the n-type and p-type thermoelectric converters placed in juxtaposition. The electrodes on the upper end portions of the thermoelectric converters are connected and united. The electrodes on the lower end portions of the thermoelectric converters are separated. A direct current is applied between the electrodes on the lower end portions from a power supply, thereby giving a heat absorbing function to an electrode (heat absorbing portion 31) while giving a heat generating function to an electrode (heat dissipation portion 33).

Figure 3:
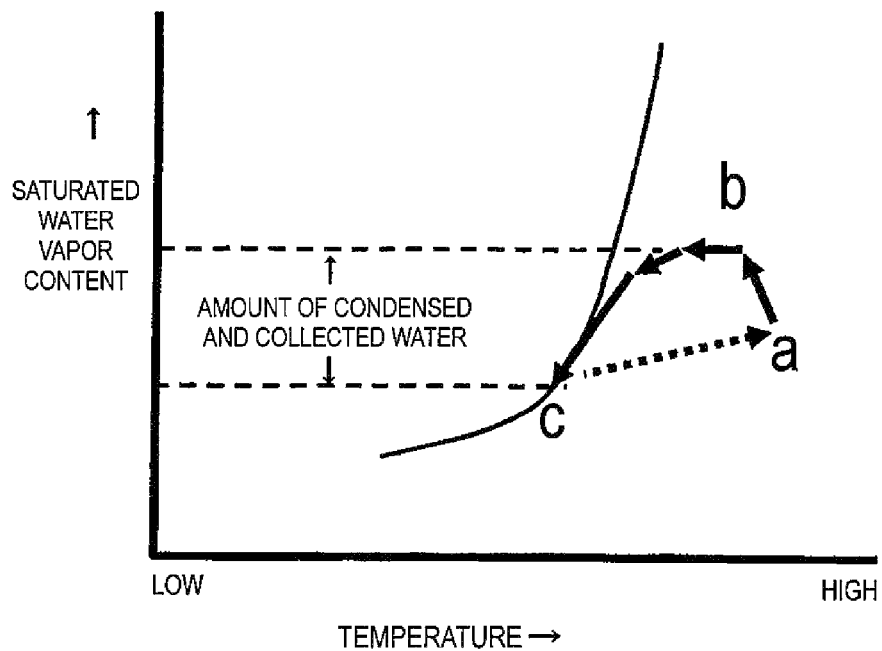
FIG. 3 is an explanatory view of relationships between temperatures and their corresponding saturated water vapor contents about air taken in, purified air, and air after condensation and collection.

FIG. 3 is an explanatory view of relationships between temperatures and saturated water vapor contents about air taken in, purified air, and air after condensation and collection.

In FIG. 3, "a" shows the temperature and saturated water vapor content about air taken in at a position "a" shown in FIG. 2. "b" shows the temperature and saturated water vapor content about purified air at a position "b" shown in FIG. 2. "c" shows the temperature and saturated water vapor content about air after condensation and collection at a position "c" shown in FIG. 2.

The temperature "a" of the air taken in decreases to the temperature shown as "b" after being purified. The temperature of the purified air further decreases to the temperature shown as after condensation and collection of moisture therefrom. The amount of condensed water to be collected is a difference in amount between saturated water vapor contents corresponding to the temperatures b and c.

The electric device 1A of the present invention uses condensed water collected from air to generate ozone water, thereby eliminating the need, for example, for water feed by a user. This makes a water feeding unit unnecessary while saving time and labor.

Third Embodiment of Electric Device of Present Invention

Figure 6:
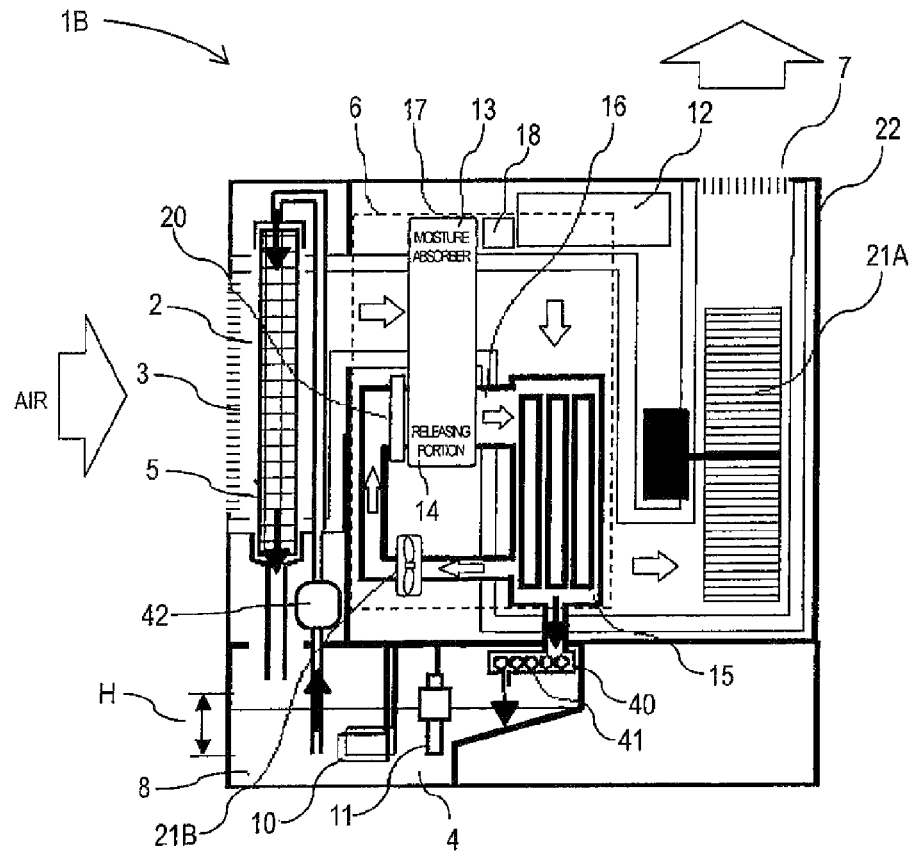
FIG. 6 is an explanatory view of an embodiment of an air cleaner of the present invention.
Figure 7:
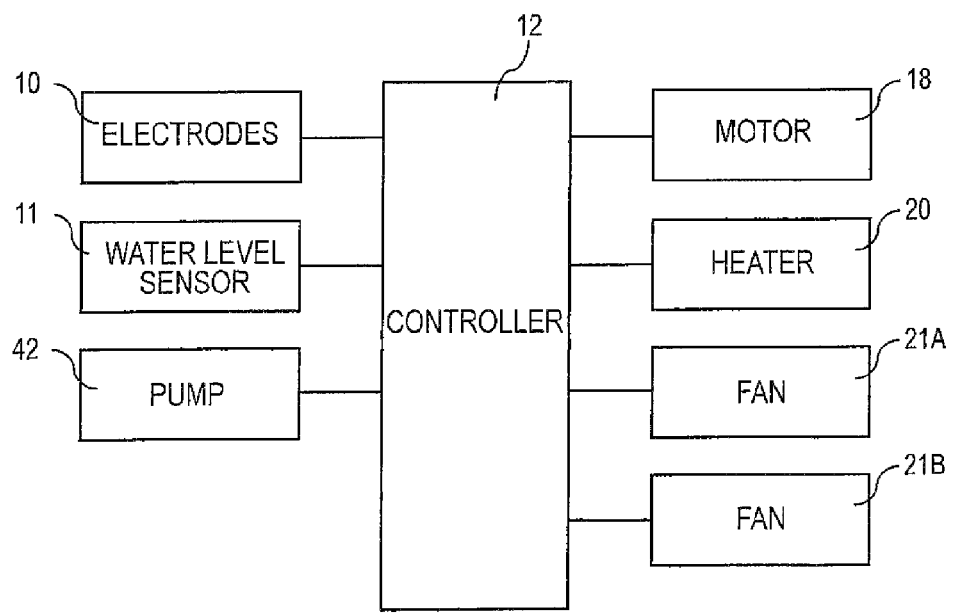
FIG. 7 is a control block diagram of the air cleaner of the present invention.

FIG. 6 is an explanatory view of an embodiment of an air cleaner of the present invention.

As shown in FIG. 6, an air cleaner 1B of the present invention includes: an air inlet 3 through which foil air is taken in to travel in a direction indicated by blank arrows; a gas-liquid contact portion 5 for making gas-liquid contact between the air taken in and electrolyzed water 4 to purify the air; a water collecting portion 6 for collecting moisture in the air after the gas-liquid contact; a fan 21A (air blowing means) for transferring the air from which the moisture was collected to an air outlet; and an air outlet 7 through which the air is ejected. The air inlet 3, the gas-liquid contact portion 5, the water collecting portion 6, the fan 21A, and the air outlet 7 are arranged in sequential order from upstream of an air duct 2.

The air cleaner 1B of the present invention further includes: a water storage portion 8 in which the collected water is stored; a pump 42 for feeding the water stored in the water storage portion 8 to the gas-liquid contact portion 5; and active oxygen species generating electrodes 10 (electrolyzing portion) for generating the electrolyzed water 4 containing an active oxygen species by electrolyzing the water stored in the water storage portion 8. The water storage portion 8 is removable. If required, a user can remove the water storage portion 8 to waste the water stored therein.

A water level sensor 11 is provided in the electrolyzed water 4 in the water storage portion 8 in order to maintain the level of the water in the water storage portion 8 within a range H of between predetermined upper and lower limits.

The upper limit is such that exceeding the height of the upper limit results in a fear of an overflow. The lower limit is such that failing to reach the height of the lower limit results in a fear that electrolysis will be made impossible and cannot be conducted well due to insufficient immersion of the electrodes 10 in the water.

Reference numeral 12 indicates a controller. In response to a signal from the water level sensor 11, the controlling portion 12 controls the number of revolutions of a rotor 17 for causing the foregoing moisture absorber 13 to rotate, ON and OFF of the pump 42, energization of the electrodes 10 (ON and OFF of an electrolyzing operation), input to a heater 20, and the like. Specifically, if the water level sensor 11 crosses the upper limit, the controlling portion 12 stops rotation of the rotor 17. If the water level sensor 11 crosses the lower limit, the controlling portion 12 causes the rotor 17 to rotate and stops energization of the electrodes 10, thereby maintaining the level of the water in the water storage portion 8 within a predetermined range.

The controlling portion 12 (conductivity detecting means) causes a certain test current to flow between the electrodes 10 at a predetermined time during an electrolyzing operation. Based on the value of a voltage applied between the electrodes 10, the controlling portion 12 determines the conductivity of the water stored in the water storage portion 8.

The water collecting portion 6 is described next.

The water collecting portion 6 includes an air circulation duct 16. The air circulation duct 16 causes moisture absorbed by the moisture absorber 13 to be released at a releasing portion 14, and causes a cooling portion (condenser) 15 to cool and condense air containing the released moisture to collect the moisture in the air. The air circulation duct 16 thereafter causes the air to circulate in a direction indicated by blank arrows. Reference numeral 21B indicates a fan for air transfer.

More specifically, the water collecting portion 6 transfers air after gas-liquid contact at the gas-liquid contact portion 5 through the air duct 2 in the direction of blank arrows. Further, the water collecting portion 6 includes the moisture absorber 13 rotatably placed at an appropriate position in the air duct 2, and the releasing portion 14. The moisture absorber 13 absorbs moisture in the transferred air. The releasing portion 14 causes the moisture absorber 13 to rotate to move to the position of the releasing portion 14, and heats the moisture absorbed by the moisture absorber 13 to release the moisture, thereby recovering the moisture absorber 13.

The cooling portion (condenser) 15 of the air circulation duct 16 cools the air circulation duct 16 from outside with air that is cooled as a result of generation of evaporation heat generated when moisture in the air evaporates after the air makes gas-liquid contact with the electrolyzed water 4 at the gas-liquid contact portion 5. Then, the cooling portion 15 cools the air containing moisture released at the releasing portion 14 to condense the moisture in the air.

Condensed water obtained from air contains no ions and has low conductivity accordingly. Meanwhile, the electrolysis mentioned above using electrodes requires a direct voltage of about 60 V that is a relatively high voltage for household electric appliances. Accordingly, in order to reduce a voltage required for electrolysis, ions such as chlorine ions should be added to increase conductivity. If the aforementioned ozone electrodes are used to generate ozone, condensed water containing halogen ions such as chlorine ions is known for its better efficiency of ozone generation.

In response, in this embodiment, condensed water is caused to flow in a sustained-release material holding portion 41 housing multiple sustained-release materials 40 that gradually release chlorine ions after contacting moisture. Then, the chlorine ions are mixed in the condensed water to increase the conductivity of the condensed water.

More specifically, condensed water is caused to flow downward toward the sustained-release material holding portion 41 placed below the air circulation duct 16. The sustained-release materials 40 are spherical substances of a diameter of about 10 mm, including mineral salt (such as sodium chloride) and grease (such as paraffin wax) surrounding the mineral salt. The sustained-release materials 40 gradually release mineral salt from between the grease after contacting moisture. In this embodiment, as a result of contact with condensed water, sodium chloride is gradually released from between paraffin wax into the condensed water as chlorine ions. The condensed water containing the chlorine ions flows downward into the water storage portion 8 placed below the sustained-release material holding portion 41.

If the determined conductivity of water in the water storage portion is equal to or less than a predetermined level, the controlling portion 12 makes the water collecting portion 6 collect water. Then, the controlling portion 12 feeds water containing chlorine ions released from the sustained-release material holding portion 41 into the water storage portion 8 to increase a chlorine ion concentration. If the water level sensor 11 detects the predetermined upper limit thereafter, the controlling portion 12 makes the water collecting portion 6 stop water collection.

There is a fear of condensation of chlorine ions if the determined conductivity of water in the water storage portion is no lower than the predetermined level. In this case, the controlling portion 12 gives an alarm to a user in order to urge the user to waste the water stored in the water storage portion 8.

The water stored in the water storage portion 8 is electrolyzed to generate the electrolyzed water 4 containing an active oxygen species.

For cooling by the cooling portion 15, the air circulation duct 16 is cooled from outside with air that is cooled as a result of generation of evaporation heat generated when moisture in the air evaporates after the air makes gas-liquid contact with the electrolyzed water 4 at the gas-liquid contact portion 5. In addition to this system, an electronic system using a Peltier element, or a refrigeration circuit system using a refrigeration cycle may be used in combination, for example. Or, at least one the foregoing systems may be employed.

The moisture absorber 13 and the releasing portion 14 are provided at their predetermined positions in the rotor 17. The moisture absorber 13 and the releasing portion 14 are driven by a motor 18 to rotate about a rotary shaft 19 (not shown).

In order for the moisture absorber 13 that absorbs moisture to move to the releasing portion 14 shown in FIG. 6, the motor 18 is actuated by the controlling portion 12 to cause the rotor 17 to rotate about the rotary shaft 19, thereby moving the moisture absorber 13 to the releasing portion 14. The moisture absorber 13 having reached the releasing portion 14 is heated by the heater 20, so that the moisture absorber 13 releases the moisture, and is recovered accordingly. Then, the motor 18 is actuated again by the controlling portion 12 to cause the rotor 17 to rotate about the rotary shaft 19, thereby moving the recovered moisture absorber 13 to the predetermined position shown in FIG. 6 at which the moisture absorber 13 is reused.

Reference numeral 21A indicates a fan for air transfer. The fan 21A transfers air from which the moisture was collected to the air outlet 7. Reference numeral 22 indicates a housing in which the constituting portions are integrally placed at their predetermined positions.

(Description of Example of Water Electrolysis)

The air cleaner 1B of the present invention is configured such that air is taken in from outside space such as space in a room or closed space into the air cleaner 1B through the air inlet 3. The air taken in comes into gas-liquid contact with the electrolyzed water 4 at the gas-liquid contact portion 5 to purify the air. Then, moisture in the purified air is collected by the water collecting portion 6. The collected water is electrolyzed in the water storage portion 8 to generate the electrolyzed water 4 containing an active oxygen species such as ozone, and the purified air is ejected through the air outlet 7.

If the active oxygen species generating electrodes are ozone electrodes, on condition that water of a predetermined amount or more, more specifically water of an amount that allows immersion of the electrodes 10 (a platinum cathode and a metal oxide anode, for example) or more is stored in the water storage portion 8, a not-shown power supply energizes the electrodes 10 in response to a signal from the controlling portion 12. Then, water electrolysis is started, so that the reaction shown by the foregoing formula (1) occurs to generate ozone, and the electrolyzed water (ozone water) 4 containing the generated ozone dissolved therein is generated in the water storage portion 8.

As already described, a porous structure (porous structure with communicatively coupled pores, for example) made of a material not deteriorated seriously by electrolyzed water may be applied as a gas-liquid contact member of the gas-liquid contact portion 5. Examples of the material include polyolefin resins, PET resins, vinyl chloride resins, fluorinated resins, and ceramics resins. More specifically, the applicable gas-liquid contact member is such that it has a wide gas contact area, that it has a surface capable of getting wet with electrolyzed water, that it has a resistance to clogging, and that it allows air purification by making gas-liquid contact between air taken in from outside space and the electrolyzed water.

The pump 42 feeds the electrolyzed water (ozone water) 4 stored in the water storage portion 8 to the gas-liquid contact portion 5. In this state, air taken in through the air inlet 3 passes through the gas-liquid contact portion 5, thereby making gas-liquid contact between the air and the ozone water 4. This realizes disinfection (sterilization) and deodorization (odor removal) of the air, and removal of a suspended matter and a hazardous matter from the air, thereby purifying the air.

As shown in FIG. 6, the electrolyzed water fed to the gas-liquid contact portion 5 by the pump 42 returns to the water storage portion 8 after the gas-liquid contact.

The air cleaner 1B of the present invention uses condensed water collected from air to generate ozone water, thereby eliminating the need, for example, for water feed by a user. This makes a water feeding unit unnecessary while saving time and labor.

(Description of Example of Electrolysis by Addition of Tap Water)

The present invention can also conduct electrolysis by adding tap water into the water storage portion 8.

Tap water is added through not-shown tap water feeding means into the water storage portion 8. Then, on condition that water of a predetermined amount or more, more specifically water of an amount that allows immersion of the electrodes 10 or more is stored in the water storage portion 8, a power supply (not shown) energizes the electrodes 10 in response to a signal from the controlling portion 12. This implements water electrolysis to cause reactions shown by the foregoing formulas (2) to (5), thereby generating an active oxygen species. As a result, the electrolyzed water 4 containing the generated active oxygen species dissolved therein is generated in the water storage portion 8.

If the active oxygen species generating electrodes are hypochlorous acid generating electrodes, the electrodes 10 are electrode plates the bases of which are made of Ti (titanium), and the coating layers of which are made of Ir (iridium) and Pt (platinum), for example. A current of a value of 10 mA (milliamperes)/cm$^2$ (square centimeter) under a constant current density is applied to the electrodes, thereby generating free residual chlorine of a predetermined concentration (1 mg (milligram)/1 (liter), for example).

This structure generates HClO (hypochlorous acid) having strong sterilizing power through the energization between the electrodes 10. The pump 42 feeds the electrolyzed water 4 containing the generated HClO (hypochlorous acid) dissolved therein to the gas-liquid contact portion 5 to which air taken in through the air inlet 3 is fed. This prevents propagation of bacteria, and inactivates viruses and allergens floating in air passing through the gas-liquid contact portion 5. Further, an odor reacts with hypochlorous acid in the electrolyzed water 4 to be ionized and then dissolved while air passes through the gas-liquid contact portion 5. Thus, the odor is removed from the air to deodorize the air.

As shown in FIG. 6, the electrolyzed water fed to the gas-liquid contact portion 5 by the pump 42 returns to the water storage portion 8 after the gas-liquid contact.

In the foregoing description, electrolysis of condensed and collected water, and electrolysis by adding tap water are shown as examples. In the present invention, these ways of electrolysis may be applied alone, or may be applied in combination. Combined use thereof more effectively prevents propagation of bacteria, more effectively inactivates viruses and allergens, and realizes more effective deodorization.

EXAMPLES

The present invention is described in more detail by introducing Examples and Comparative Examples. However, the present invention is not intended to be limited to these Examples.

Example 1

Outside space with room-temperature air was prepared that has an odor containing all ingredients of a finished cigarette per cubic meter. The odor in this state is defined as 100%. An experimental electric device of the structure of the present invention shown in FIG. 2, and an experimental air cleaner of the structure of the present invention shown in FIG. 6 were started to make gas-liquid contact between the air in the outside space and electrolyzed water (of a chlorine concentration of 10 mg/L), thereby removing the odor from the air.

Figure 4:
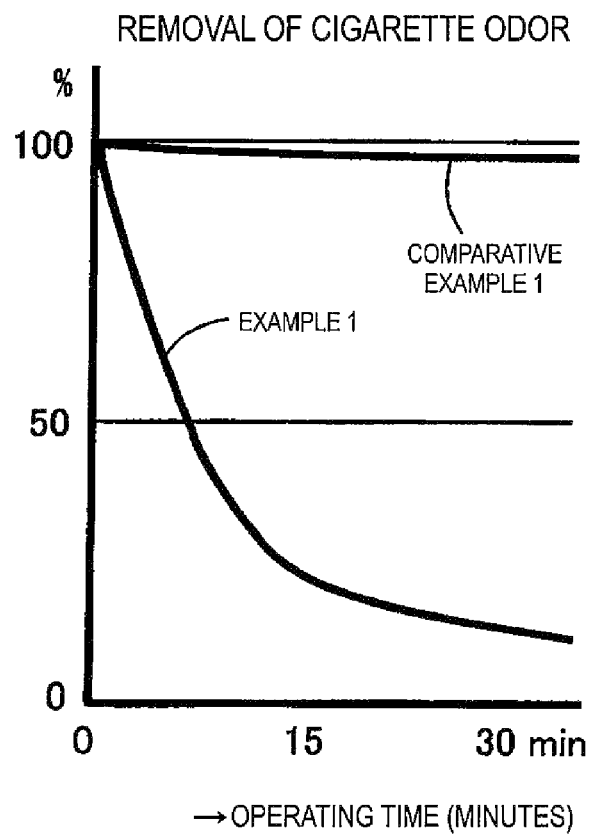
FIG. 4 is an explanatory view of a relationship between a cigarette odor and the operating time of the electric device of the present invention when air is purified by the electric device.

A result of the experiment is shown in FIG. 4.

It is seen from FIG. 4 that running the electric device and the air cleaner of the present invention realizes rapid odor removal in about 15 minutes.

Comparative Example 1

The same experiment as that in Example 1 was conducted for comparison, except that the electric device and the air cleaner of the present invention were not used and were left standing. A result of the experiment is shown in FIG. 4. It is seen from FIG. 4 that, in this case, the odor was not removed even after elapse of 30 minutes.

Example 2

Outside space with room-temperature air was prepared that has uniformly floating $1 \times 10^8$ lactic acid bacteria (genus Bacillus) per cubic meter. The state of air containing these floating bacteria is defined as 100%. An experimental electric device of the structure of the present invention shown in FIG. 2, and an experimental air cleaner of the structure of the present invention shown in FIG. 6 were started to make gas-liquid contact between the air in the outside space with electrolyzed water (of a chlorine concentration of 10 mg/L), thereby sterilizing the air.

Figure 5:
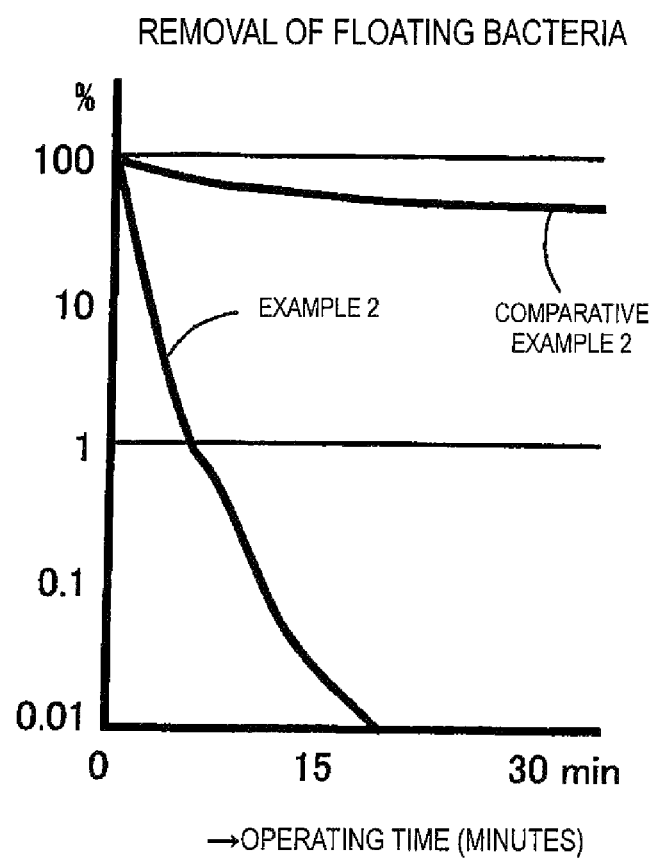
FIG. 5 is an explanatory view of a relationship between floating bacteria and the operating time of the electric device of the present invention when air is purified by the electric device.

A result of the experiment is shown in FIG. 5. It is seen from FIG. 5 that running the electric device and the air cleaner of the present invention realizes complete sterilization in about 15 minutes.

Comparative Example 2

The same experiment as that in Example 2 was conducted for comparison, except that the electric device and the air cleaner of the present invention were not used and were left standing. A result of the experiment is shown in FIG. 5. It is seen from FIG. 5 that, in this case, the state at the start of the experiment was maintained and air was not sterilized even after elapse of 30 minutes.

The description of the embodiments given above are intended to explain the present invention, and are not intended to limit the present invention, or the scope of the present invention recited in claims. Further, the constituent parts of the present invention are not limited to those described in the embodiments. Various modifications and variations thereof can be devised without departing from the technical scope of claims.

(1) In the foregoing embodiments, examples of a water collecting portion shown are the one using a desiccant, and the one using a Peltier element. However, the water collecting portion is not limited to these, as long as it allows use of condensed water collected from air.

As another specific example, the water collecting portion may employ a refrigeration circuit system using a refrigeration cycle.

(2) The following exemplary means may be provided in order to remove an active oxygen species such as ozone from air ejected through the air outlet of the electric device and the air cleaner of the present invention described in the embodiments: active oxygen species removing means for decomposing and removing ozone by making the ozone contact with an ozone decomposition catalyst; active oxygen species removing means for decomposing and removing ozone by making the ozone exposed to ultraviolet radiation; and active oxygen species removing means for removing ozone by making an absorber or a desiccant absorb or suck the ozone.

If a sensor determines that ozone of a concentration equal to or greater than a predetermined level is contained in air ejected through the air outlet of the electric device and the air cleaner of the present invention, ozone removing means may be started in response to a signal from the controller. Thus, the level of ozone can be reduced to a safe level, or the ozone can be removed completely.

(3) In the foregoing embodiments, in the electric device of the present invention with the water collecting portion using a Peltier element, air comes into contact with a heat dissipation portion of the Peltier element, thereby heating the air. The heated air is thereafter subjected to temperature control. However, use of the heat dissipation portion of the Peltier element is not limited to this way.

As another specific example, the heat dissipation portion can be used to raise the temperature of water stored in the water storage portion.

Industrial Applicability

The electric device and the air cleaner of the present invention are configured such that air taken through the air inlet is collected by the water collecting portion. The collected water is stored in the water storage portion, and the water stored in the water storage portion is electrolyzed to generate electrolyzed water containing an active oxygen species such as ozone. The air taken in comes into gas-liquid contact with the electrolyzed water at the gas-liquid contact portion to purify the air, and then the purified air is ejected. This realizes a remarkable effect since air is cleaned without requiring additional water feed and without generating a by-product, and size and cost reductions, and long-term stable use are realized. Further, increasing humidity by making gas-liquid contact of the air taken in leads to a higher rate of water collection even in the case of low humidity as a result of a small amount of moisture in the air taken in through the air inlet, for example. Also, the gas-liquid contact between the air and the electrolyzed water at the gas-liquid contact portion causes moisture to evaporate, and generation of resultant evaporation heat cools the air. Thus, if the cooled air is used for water collection at the water collecting portion, this produces a remarkable effect since a rate of water collection is increased to a higher level. Thus, the electric device and the air cleaner of the present invention are of great industrial usefulness.

The invention claimed is:

1. An electric device, comprising: an air inlet through which air is taken in; a gas-liquid contact portion for making gas-liquid contact between the air taken in and electrolyzed water to purify the air; a water collecting portion for collecting moisture in the air after the gas-liquid contact; an air outlet through which the air in which the moisture was collected is ejected, wherein the air inlet, the gas-liquid contact portion, the water collecting portion, and the air outlet are arranged in sequential order from upstream of an air duct; a water storage portion in which the gas-liquid contact portion is dipped and in which the water collected by the water collecting portion is stored; and an electrolyzing portion for generating the electrolyzed water containing an active oxygen species by electrolyzing the water stored in the water storage portion.

2. The electric device according to claim 1, wherein the water collecting portion comprises: a moisture absorber for absorbing moisture in the air after the gas-liquid contact; a releasing portion for heating the moisture absorbed by the moisture absorber to release the moisture; and a cooling portion for cooling and condensing the released moisture with the air after the gas-liquid contact to collect the moisture, and wherein the water collected after the cooling and condensation is stored in the water storage portion.

3. The electric device according to claim 1, comprising a controlling portion for maintaining a water level of the water stored in the water storage portion within a predetermined range.

4. The electric device according to claim 1, comprising active oxygen species removing means for removing an active oxygen species from air ejected through the air outlet.

5. The electric device according to claim 1, wherein: the water collecting portion uses a Peltier element; the air after the gas-liquid contact comes into contact with a heat absorbing portion of the Peltier element to condense and collect moisture in the air; and the air from which the moisture was collected comes into contact with a heat generating portion of the Peltier element and is controlled in temperature, where necessary, and which is thereafter ejected.

6. The electric device according to claim 2, comprising:
a controlling portion for maintaining a water level of the water stored in the water storage portion within a predetermined range;
active oxygen species removing means for removing an active oxygen species from air ejected through the air outlet; and wherein: the water collecting portion uses a Peltier element; the air after the gas-liquid contact comes into contact with a heat absorbing portion of the Peltier element to condense and collect moisture in the air; and the air from which the moisture was collected comes into contact with a heat generating portion of the Peltier element and is controlled in temperature, where necessary, and which is thereafter ejected.

* * * * *